United States Patent [19]

Müller et al.

[11] 4,018,833
[45] Apr. 19, 1977

[54] PREPARING RESORCINOLS FROM δ-KETOCARBOXYLIC ACIDS OR FROM THEIR LACTONES

[75] Inventors: Werner Heinrich Müller, Kelkheim, Taunus; Hans Fernholz, Fischbach, Taunus, both of Germany

[73] Assignee: Hoechst Aktiengesellschaft, Frankfurt am Main, Germany

[22] Filed: Oct. 20, 1975

[21] Appl. No.: 624,290

[30] Foreign Application Priority Data

Oct. 22, 1974   Germany .......................... 2450086

[52] U.S. Cl. .................. 260/621 R; 260/619 R; 260/619 D; 260/620; 260/625; 260/586 C
[51] Int. Cl.² .................................... C07C 37/00
[58] Field of Search .......... 260/619 R, 620, 621 R, 260/625, 619 D

[56] References Cited

UNITED STATES PATENTS

| 3,931,322 | 1/1976 | Hengartner et al. | 260/586 C |
| 3,932,510 | 1/1976 | Muller | 260/586 C |
| 3,932,511 | 1/1976 | Schaafsma et al. | 260/586 C |
| 3,950,438 | 4/1976 | Schaafsma et al. | 260/586 C |

OTHER PUBLICATIONS

Mannich, et al., "Ber.," vol. 71, pp. 2090–2091, (1938).
Kost et al., "Zhur, Obsch. Khim," 32:3983–3986, (1962).
Vorländer et al., "Ann.," 294:270–271.
Bornstein et al., "Chem. Ab.," 48:9933e, (1954).
Schusherma, et al., "Chem. Ab.," 66:94714x, (1967).

*Primary Examiner*—Norman Morgenstern
*Attorney, Agent, or Firm*—Curtis, Morris & Safford

[57] ABSTRACT

Process for preparing resorcinols from δ-ketocarboxylic acids or their lactones in the gaseous phase at temperatures from 150°–500° C by means of a dehydrogenation catalyst.

12 Claims, No Drawings

PREPARING RESORCINOLS FROM δ-KETOCARBOXYLIC ACIDS OR FROM THEIR LACTONES

It has been suggested that δ-ketocarboxylic acids may be transformed in the gaseous phase by catalytic dehydration, into cyclohexane-1,3-diones, which are then converted by dehydrogenation to technically important resorcinols.

These processes which start from free δ-ketocarboxylic acids, in comparison to all processes starting from δ-ketocarboxylic acid esters, have in common the advantage that the free δ-ketocarboxylic acids are easily accessible by direct addition of acrylic acids to ketones.

However, for successfully carrying out said processes, it is essential that their esters must be obtainable either by subsequent esterification of these acids or by addition of acrylic esters to ketones, the acrylic esters may be obtained first by esterification of acrylic acids. Using free δ-ketocarboxylic acids instead of their esters means in any case one reaction step less, a fact which represents a considerable technical progress especially due to reduced investment costs.

Nevertheless, this two-stepped transformation of free δ-ketocarboxylic acids into resorcinols brings about the disadvantage that the cyclohexanediones being formed as intermediate products are obtained at poor concentration rates upon catalytic dehydration, and that they must be isolated by a costly and cumbersome separation prior to their being incorporated into the subsequent liquid-phase dehydrogenation.

The present invention aims, therefore, at a method for avoiding said separating operation.

A process has now been found for preparing resorcinols of general formula

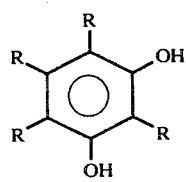

wherein the individual radicals R may be identical or different and may represent each hydrogen atom, an alkyl group, a cycloalkyl group, or an aryl group having up to 12 carbon atoms each, which comprises that a δ-ketocarboxylic acid of general formula

R—CH$_2$—CO—CH(R)—CH(R)—CH(R)—COOH or its lactone of general formula

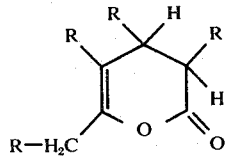

wherein R has the afore mentioned meaning, is contacted in the gaseous phase with a dehydrogenation catalyst at temperatures of from 150°–500° C, and that subsequently separating resorcinol is from the reaction mixture. The δ-ketocarboxylic acids are equilibrated to δ-enolic lactones according to the following equation (scheme):

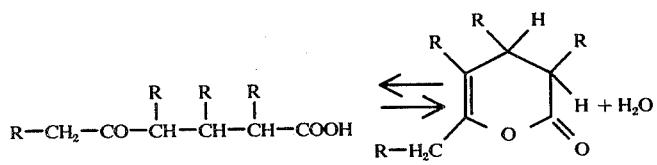

For lower temperatures this equilibrium centers on the left, for higher temperatures it is shifted in the direction to the enolic lactones. The speed at which the equilibrium is settling, depends however on the dehydrogenation catalyst employed.

The substituents R in the starting compounds may be identical or different and may represent each a hydrogen atoms, an alkyl group, a cycloalkyl group or an aryl group having up to 12 carbon atoms each. Possible suitable alkyl groups — which may be straight-chained or branched — can be, for example; methyl, ethyl, propyl, butyl, pentyl, hexyl, octyl, decyl, dodecyl; as suitable cycloalkyl groups may be cited: cyclopentyl, cyclohexyl, cyclodecyl, cyclododecyl. Preference is given to the use of alkyl radicals or cycloalkyl radicals having up to 6 carbon atoms, preferred aromatic radicals being the phenyl group and the naphtyl group.

Especially suitable are 5-oxohexanoic acid, 5-oxoheptanoic acid, 4-methyl-5-oxoheptanoic acid, 4-propyl-5-oxohexanoic acid, 4-hexyl-5-oxohexanoic acid, 3-methyl-5-oxohexanoic acid and 5-oxononanoic acid and the corresponding δ-enolic lactones.

Surprisingly, the δ-ketocarboxylic acids in the gaseous phase may be transformed to the corresponding resorcinols at good yields, since this reaction does not materialize in the liquid phase.

Suitable dehydrogenation catalysts are those, for example, which contain a metal or a compound of a metal of the 8$^{th}$ or 1$^{st}$ subgroup of the periodic table or of mixtures thereof. Especially suitable are palladium, platinum, ruthenium, rhodium, nickel and copper.

These catalyst are generally used on carriers such as carbon, aluminum oxide, silica acid, magnesium oxide, calcium oxide, aluminum phosphate, boron trioxide, chromium trioxide, zirconium oxide, asbestos, boron phosphate, spinels (such as spinels of lithium, magnesium, cobalt, manganese or zinc-aluminum) or other mixed oxides preferably Pd and/or platinum on Al$_2$O$_3$, SiO$_2$, carbon or a spinel.

The catalytically active substances are applied at the rate of from 0.1 to 20 weight %, calculated on the weight of the carrier, preferably from 0.2 to 10%.

Said catalyst may be activated by adding catalysts according to Friedel-Crafts, such as polyphosphoric acid, $AlCl_3$, $ZnCl_2$, $FeCl_3$, $SbCl_3$.

The catalysts may be applied in a fixed bed or in a fluidized bed.

The process of the invention provides for conveying the starting composition in its gaseous state, preferably diluted by a carrier gas such as nitrogen, carbon dioxide or hydrogen or by an easily volatile solvent such as water, alcohols, ethers or short-chained organic acids, over the catalyst heated to 100°–500° C, preferably to 250°–420° C. The use of hydrogen has an especially favorable effect on the life span of the catalyst. Subsequently, the products are condensed and worked up, e.g. by distillation or by extraction.

The pressure is not of critical importance to the process according to the invention, which is generally carried out within a range of from 10 millibars to 10 bars. But, keeping the partial pressure of the hydrogen which is formed during the reaction below 1 bar, is advantageous so as to avoid hydrations and hydrogenolyses of the intermediate products and the final products. The residence time of the reaction gases in the contact layer varies from 0.1 to 5 seconds, but longer or shorter residence periods are also possible. The starting products may be evaporated either undiluted or combined with water, acetic acid, benzene, hexane, acetone, isopropanol or with a different solvent or mixture of solvents and conveyed over the catalyst, optionally together with a carrier gas, e.g. nitrogen, hydrogen, carbon dioxide, or methane. The resorcinols prepared according to the invention are utilized for the manufacture of dyestuffs, resorcinol-formaldehyde resins and wood glues.

The following Examples illustrate the invention:

which showed constant values upon two to four hours after the reaction start.

The products were identified by gaschromatographical comparison with comparative material being synthetized otherwise, by means of combining gas chromatography and mass spectroscopy, and by NMR spectra.

EXAMPLE 1

The above specified reactor contains 100 ml of a catalyst consisting of 2 weight % of Pd on a lithium-aluminum spinel being shaped as 3 mm pellets. For activating the catalyst, it is heated for 3 hours to 300° C in a nitrogen-hydogen-current (34 l of $N_2$, 10 l of $H_2$ per hour).

At a temperature of 300° C a quantity of 22.5 g. of 5-oxohexanoic acid and 34 l of $H_2$ were introduced per hour into the evaporator which had been preheated to 350° C and conveyed from here over the catalyst. After an operation period of 4 hours the reaction product which was fomed during 1 hour (22 g) contained 10 weight % of resorcinol, 2 weight % of cyclohexanedione, 1.5 weight % of phenol, 1.3 weight % of cyclohexanone, 0.3 weight % of methylpropylketone, 80 weight % of 5-oxohexanoic acid and 2.4 weight % of $H_2O$.

Calculated on reacted 5-oxohexanoic acid, the selectivity of resorcinol amounts to 58.9 mole %, of cyclohexanedione 11.6 mole % and of phenol 9.3 mole %.

EXAMPLES 2 – 4

In these cases the catalyst consists of 2% of Pd metal on a commercially available δ-aluminum oxide (99.8% of $Al_2O_3$). 22.5 g of 5-oxohexanoic acid together with 34 l of $H_2$ are conveyed per hour over the catalyst, at temperatures comprised between 290° and 315° C. Table 1 specifies the results.

TABLE 1

| Example No. | Temperature (° C) | Quantity (g) | REACTION PRODUCT Composition | | | | | | Selectivity (mole%) | | |
|---|---|---|---|---|---|---|---|---|---|---|---|
| | | | OHS[1] | Resorcinol | CD[2] | φ-OH[3] | MPK[4] | $H_2O$ | Res[5] | CD[2] | φ-OH[3] |
| 2 | 290 | 22.3 | 84.8 | 7.5 | 2.0 | 1.0 | 0.8 | 1.9 | 54.5 | 14.7 | 8.6 |
| 3 | 300 | 22.1 | 74.2 | 16.2 | 1.8 | 1.8 | 1.7 | 4.0 | 73.0 | 8.3 | 9.8 |
| 4 | 315 | 22.0 | 72.0 | 15.8 | 2.0 | 2.5 | 2.0 | 4.5 | 65.2 | 8.2 | 9.8 |

[1]OHS = oxohexanoic acid
[2]CD = cyclohexanedione-1,3
[3]φ-OH = phenol
[4]MPK = methylpropylketone
[5]Res = Resorcinol

EXAMPLES

The tests as per the following Examples were carried out in such a way that the starting products were first transferred to the evaporator device heated to 350° C — together with the diluent — and then conveyed through the glass reactor (70 cm length, 2 cm diameter). The glass tube was heated by means of an electric oven. The center of this glass tube was charged with a catalyst layer 25 cm thick (100 ml). The temperature was measured on various spots by thermocouples set up in a glass core which itself was placed in the center of the reactor device. The grains of the catalyst had a diameter of from 1 to 3 mm. The reaction gases were condensed in two traps cooled to −80° C and placed behind the reactor.

At intervals of from half an hour to 1 hour product samples were withdrawn and submitted to a gas-chromatographical analysis. The final evaluation was based on such samples only, the concentration ratios of

EXAMPLE 5

The test provided, for spreading 2% of Pd as $PdCl_2$ on a commercially available carrier, namely $SiO_2/Al_2O_3$ (87 weight %/13 weight %) and for subsequently reducing it with a 25% aqueous solution of hydrazine. 100 ml of the catalyst were charged after drying into the above described apparatus and submitted to additional activation for 2 hours at 300° C in a current of nitrogen ($N_2$) (at the rate of 34 l/hour) and hydrogen ($H_2$) (at the rate of 10 l/hour).

An hourly rate of 30 g (0.23 mole) of 5-oxohexanoic acid of 34 l of $N_2$ and of 10 l of $H_2$ was conveyed over the catalyst heated to 300° C. The reaction product (29 g) contained 10.1 weight % of resorcinol, 2.5 weight % of cyclohexanedione, 20 weight % of 6-methyl-3,4-dihydro-2-pyranone, 55 weight % of $H_2O$, 57 weight % of non-reacted acid and 1.5 weight % of phenol, 1.0 weight % of 6-methylpryanone-(2) and 0.8 weight % of methylpropylketone. At a reaction of 43 mole % of 5-oxohexanoic acid the selectivity of resorcinol amounted to 27.8 mole %, the selectivity of cyclohexanedione was 7.0 mole % and the selectivity of δ-enol lactone was 55.0 mole %. This latter composition — while resting — being transformed entirely back to 5-oxohexanoic acid by hydrolysis with the reaction water, the selectivity of resorcinol — calculated on consumed 5-oxohexanoic acid equivalents — amounted to 62 mole % and the selectivity of cyclohexanedione was 16 mole %.

EXAMPLE 6

2% of Pd as $PdCl_2$ and 2% of Na as NaCl were spread onto a commercially available carrier (89–90% of $SiO_2$, 6% of $Al_2O_3$, 6% of $Fe_2O_3$), then reduced with a 20% aqueous hydrazine solution. After drying another 3 weight %, of $FeCl_3$ were applied. 100 ml of the catalyst were activated for 2 hours at 250° C in the afore described apparatus in a current of $H_2/N_2$ (10 l of $H_2$/30 l of $N_2$ per hour).

Subsequently 34 l of hydrogen and 22.5 g of 5-oxohexanoic acid were conveyed per hour through the evaporator heated to 350° C and then through the catalyst layer having a temperature of 275° C.

The reaction product (22 g) contained 12 weight % of resorcinol, 4 weight % of cyclohexanedione, 10.5 weight % of δ-enol lactone, 3.8 weight % of $H_2O$, 65 weight % of 5-oxohexanoic acid and some methylpropylketone, hexanoic acid, cyclohexanone and phenol. The selectivity of resorcinol was 61.3 mole %, the selectivity of cyclohexanedione amounted to 20.4 mole % — calculated on consumed 5-oxohexanoic acid equivalents.

EXAMPLES 7 – 9

The catalyst contained 2% of Pd and 0.5% of Pt on the commercial aluminum oxide described by the examples 2–4. 45 g of δ-ketocarboxylic acid and 34 l of hydrogen per hour were conveyed over 100 ml of this catalyst at 300° C. The results are specified in scheme 1 and table 2 as follows:

TABLE 2-continued

| Example | δ-ketocarboxylic acid (I) with | | con-version rate (mole %) | selectivity (mole %) of the products | | | | |
|---|---|---|---|---|---|---|---|---|
| | $R^1$ | $R^2$ | | II x | II xx | III x | III xx | IV x | IV xx |
| 9 | $CH_3$ | H | 63 | 31 | 38.8 | 43 | 53.8 | 20 | — | x calculated on reacted δ-ketocarboxylic acid
xx calculated on reacted δ-ketocarboxylic acid equivalents

EXAMPLE 10

50 ml of a catalyst consisting in 10% of Pd on carbon as extrusion products (diameter 2.5 mm, length 5 mm) were charged into the afore described reactor and activated by conveying a nitrogen/hydrogen current (34 l of nitrogen $N_2$ and 10 l of hydrogen $H_2$ per hour) at 300° C for 5 hours. Subsequently, while maintaining the hydrogen current, 10 g of 5-oxohexanoic acid and 10 g of $H_2O$ in their gaseous state were conveyed per hour over the catalyst having a temperature of from 320° to 325° C. After an operational period of several hours, a product sample of a 2-hours' period (40 g) was collected in a receiver cooled to −30° C. The analysis of this product showed the following composition: 52.1 weight % of $H_2O$, 24.5 weight % of 5-oxohexanoic acid, 13.5 weight % of resorcinol, 2.4 weight % of cyclohexanedione, and some phenol, methylpropylketone, hexanoic acid and cyclohexanone. The selectivity of resorcinol was 69 mole % and that of cyclohexanedione was 12.6 mole % calculated on reacted 5-oxohexanoic acid equivalents.

What is claimed is:

1. A process for the preparation of resorcinol of the formula

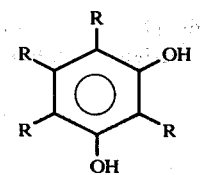

wherein each of the R substituents may be the same or different and is a member selected from the group consisting of H and alkyl, cyclo alkyl and aryl having up to 12 carbon atoms, which comprises contacting a ketocarboxylic acid of the formula Scheme 1

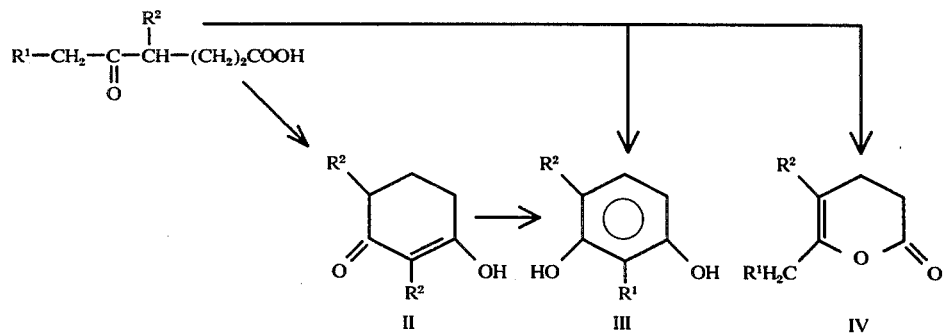

TABLE 2

| Example | δ-ketocarboxylic acid (I) with | | con-version rate (mole %) | selectivity (mole %) of the products | | | | | |
|---|---|---|---|---|---|---|---|---|---|
| | $R^1$ | $R^2$ | | II x | II xx | III x | III xx | IV x | IV xx |
| 7 | $CH_3$ | $CH_3$ | 55 | 7 | 8.6 | 70 | 86.4 | 19 | — |
| 8 | H | $CH_3$ | 53 | 29 | 32.6 | 45 | 50.6 | 21 | — |

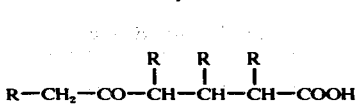

or its lactone of the formula

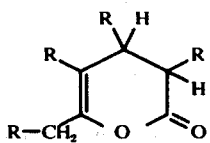

wherein R has the aforesaid meaning, with a dehydrogenation cayaltyst selected from the group consisting of a metal or a compound of a metal from the eighth or first subgroup of the periodic table and a carrier therefore, said contacting being carried out in a gaseous phase and at a temperature of 150° to 500° C, dehydrogenating said ketocarboxylic acid or said lactone to obtain said resorcinol, cooling and condensing said gas phase and recovering said resorcinol from said condensate.

2. Process according to claim 1, which comprises that the catalyst contains a metal of the 8th subgroup.

3. Process according to claim 1, which comprises that the catalyst is activated by the addition of a Friedel-Crafts catalyst.

4. Process according to claim 1, which comprises the dilution of the initial materials with hydrogen, nitrogen, $CO_2$ or water and their being conveyed over the catalyst.

5. Process according to claim 1, which comprises that the operations are carried out at temperatures of from 250° to 420° C.

6. the process of claim 1 wherein said carrier is a member selected from the group consisting of carbon, aluminum oxide, silicic acid, mangesium, calcium oxide, aluminum phosphate, boron trioxide, chromium trioxide, zirconium oxide, asbestos, boron phosphate, spinels of lithium, magnesium cobalt, manganese and zinc-aluminum.

7. The process of claim 1 wherein R is a member selected from the group consisting of hydrogen, alkyl having 1 to 12 carbon atoms, cycloalkyl having 5 to 12 carbon atoms, phenyl and naphthyl.

8. The process of claim 1 wherein said catalyst is a member selected from the group consisting of palladium, platinum, ruthenium, rhodium, nickel and copper.

9. The process of claim 1 wherein the catalyst is activated by the addition of a Friedel-Crafts catalyst which is a member selected from the group consisting of polyphosphoric acid, $AlCl_3$, $ZnCl_2$, $FeCl_3$ and $SbCl_3$.

10. The process of claim 1 wherein said ketocarboxylic acid or said lactone is contacted with said catalyst in a carrier gas which is a member selected from the group consisting of nitrogen, carbon dioxide, hydrogen, methane, water, alcohols, ethers and short chain organic acids.

11. the process of claim 1 wherein the δ-ketocarboxylic acid is a member selected from the group consisting of 5-oxohexanoic acid, 5-oxoheptanoic acid, 4-methyl-5-oxoheptanoic acid, 4-propyl-5-oxohexanoic acid, 4-hexyl-5-oxohexanoic, 3-methyl-5-oxohexanoic acid and 5-oxononanoic acid and the lactone is a member selected from the corresponding δ-enolic lactones.

12. The process of claim 1 wherein the catalyst and carrier are members selected from the group of catalyst consisting of palladium, palladium chloride, palladium and platinum and carriers selected from the group consisting of lithium-aluminum spinel, γ-aluminum oxide, $SiO_2/Al_2O_3$, $SiO_2$-$Al_2O_3$-$Fe_2O_3$ and carbon.

* * * * *